United States Patent [19]

Singh et al.

[11] 4,439,616

[45] Mar. 27, 1984

[54] TERTIARY ARALKYL URETHANES AND ISOCYANATES DERIVED THEREFROM

[75] Inventors: Balwant Singh, Stamford; Laurence W. Chang, Orange; Peter S. Forgione, Stamford, all of Conn.

[73] Assignee: American Cyanamid Company, Stamford, Conn.

[21] Appl. No.: 400,799

[22] Filed: Jul. 22, 1982

[51] Int. Cl.³ ............... C07C 125/073; C07C 125/065
[52] U.S. Cl. .................................. 560/25; 260/453 P; 560/24; 560/27; 560/28; 560/29; 560/30
[58] Field of Search ........................... 560/24, 25, 27; 260/453 P

[56] References Cited

U.S. PATENT DOCUMENTS

| | | | |
|---|---|---|---|
| 3,477,933 | 11/1969 | Stamm et al. | 560/25 X |
| 3,962,302 | 6/1976 | Rosenthal et al. | 260/453 P |
| 4,130,577 | 12/1978 | Nagato et al. | 260/453 P |
| 4,379,767 | 4/1983 | Alexanian et al. | 260/453 P |

FOREIGN PATENT DOCUMENTS 625748 12/1962 Belgium .

*Primary Examiner*—Dolph H. Torrence
*Attorney, Agent, or Firm*—Gordon L. Hart; Steven J. Hultquist

[57] ABSTRACT

Production of tertiary aralkyl isocyanates, such as tetramethyl xylylene diisocyanates, by thermal cracking of corresponding urethanes formed by addition of corresponding olefins and carbamic acid esters at moderate temperatures and in the presence of acid catalyst.

25 Claims, 1 Drawing Figure

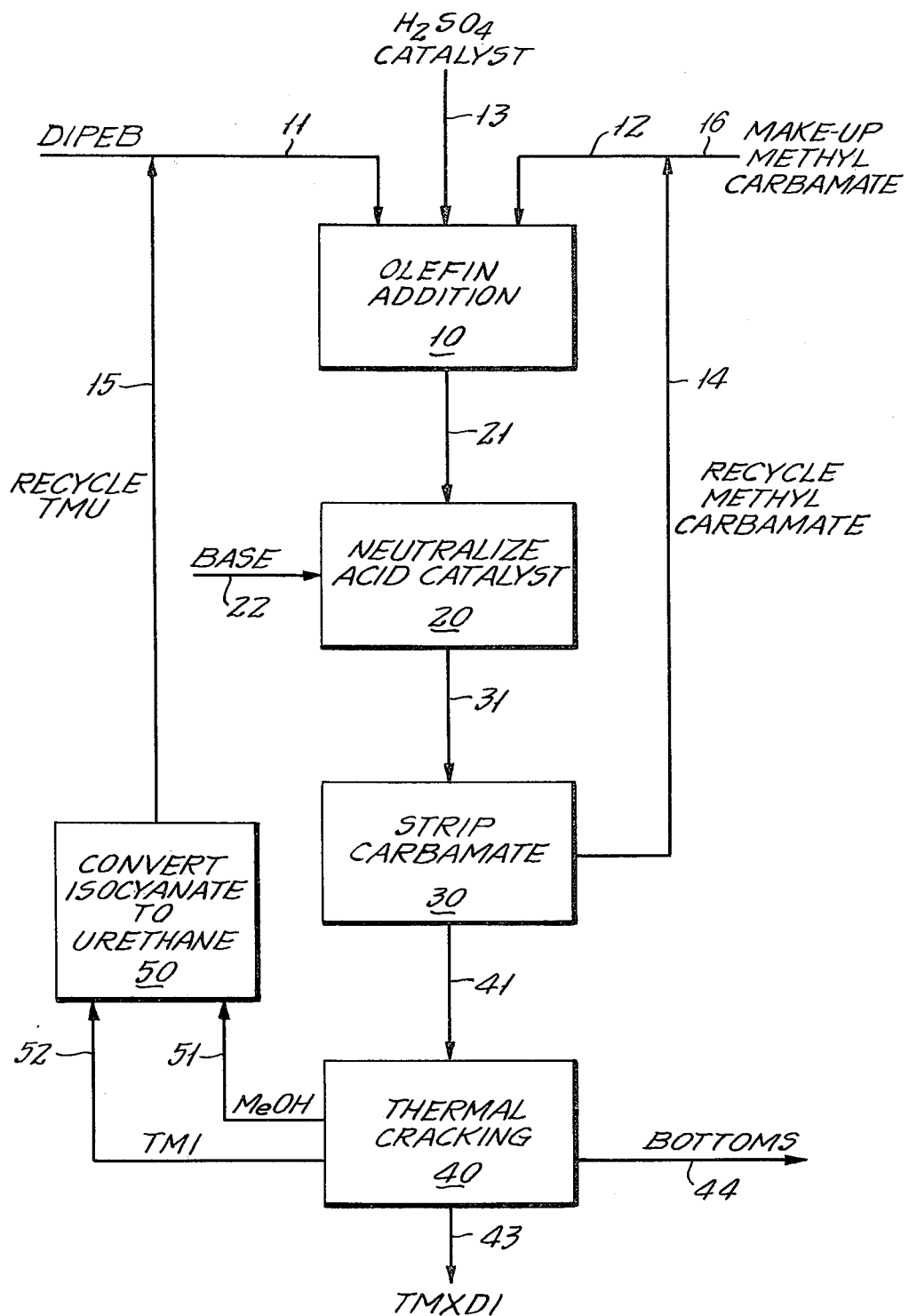

TERTIARY ARALKYL URETHANES AND ISOCYANATES DERIVED THEREFROM

This invention relates to the manufacture of isocyanates and in particular provides a new route for the synthesis of tertiary aralkyl isocyanates and also provides a valuable class of urethanes useful in the production of tertiary aralkyl isocyanates.

Isocyanates having an isocyanato group attached to a tertiary aliphatic carbon atom also having aromatic substituents, for example, meta- and para- tetramethylxylylene diisocyanates, are particularly useful for reaction with a wide variety of polyols to give urethane polymers which can be either rigid or flexible and which can be endowed with a wide variety of properties. Such urethane polymers can be formed into rigid and flexible foamed articles, sheets, high density sheets and articles of various shapes. The light stability of these urethane polymers makes them extremely useful in surface coatings and other applications where light stability is desirable, e.g. light stable RIM elastomers.

Such tertiary aralkyl isocyanates have been prepared by a variety of different reactions, such as by the phosgenation of corresponding organic amines, by reaction of corresponding olefins with isocyanic acid (U.S. Pat. No. 3,290,350), by reaction of the corresponding halides with an alkali metal isocyanate (U.S. Pat. No. 4,130,577) and by reaction of the corresponding halide with isocyanic acid (copending applications Ser. No. 333,696, filed Dec. 17, 1981, U.S. Pat. No. 4,361,518 Ser. No. 335,945 filed Mar. 8, 1982).

These various processes are diadvantageous for one or more of a variety of reasons, such as that the materials are difficult to handle or are corrosive, the yields are poor, expensive reactants are required and the products are difficult to recover.

It is an important object of this invention to produce such tertiary aralkyl isocyanates utilizing non-corrosive, low-cost starting materials in a simple process yielding the desired isocyanates whereby they are readily recovered and purified. In accordance with this invention the manufacture of a tertiary aralkyl isocyanate is by the preparation of the corresponding tertiary aralkyl carbamic acid ester of a lower aliphatic alcohol followed by the thermal cracking of such urethane to form the isocyanate and the free alcohol.

Since the esters of carbamic acid, such as methyl carbamate, the esters of substituted carbamic acids, such as the dimethyl ester of α,α,α'α'-tetramethylxylylene dicarbamic acid, and the polymers of poly isocyanates with polyols are all properly called urethanes, for the sake of clarity, herein an unsubstituted carbamic acid ester will be called "carbamate" or "carbamic acid ester;" a substituted carbamic acid ester will be called "urethane," "monourethane," "diurethane," "polyurethane" or "urethane ester;" and the polymers will be called "urethane polymers."

Urethanes which are useful in forming tertiary aralkyl isocyanates by thermal cracking in accordance with this invention are generally designated by the formulae:

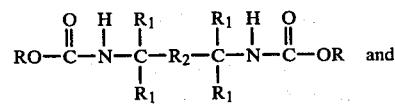 and

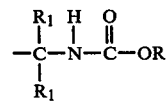

wherein R is an alkyl radial having from 1 to 18 or more carbon atoms; $R_1$ is an alkyl radical having from 1 to 3 carbon atoms; and $R_2$ represents an aromatic hydrocarbon moiety such as phenyl, biphenyl and naphthalyl and such an aromatic hydrocarbon moiety having substituents including halogen atoms, methyl and methoxy groups and substituents such as:

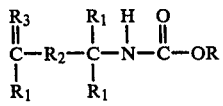

and wherein $R_3$ is an alkylidene group having from one to three carbon atoms.

These urethanes, which themselves are an important part of this invention, are thus tertiary aralkyl urethanes in which R is a radical derived from an aliphatic alcohol, such as methanol, ethanol, isopropanol, 2-ethylhexanol-1 and n-octadecanol. Such alcohol is split off on thermal cracking of the urethane ester and can usually be recovered and recycled as discussed below.

The tertiary aralkyl urethane esters of this invention can be prepared, for example, by reaction of the carbamic acid ester of a lower aliphatic alcohol and an olefin, as for example, is disclosed in Belgian Pat. No. 625,748, granted Dec. 12, 1962. As set forth in that patent the reaction of the olefin and carbamate generally proceeds at moderate temperatures in the presence of an acid catalyst.

The urethane esters of this invention are converted to the corresponding tertiary aralkyl isocyanates by thermal cracking. Yields are good, and alcohol recovery and removal are particularly high where the aliphatic alcohol group of the initial carbamic acid ester is methanol or other lower, preferably normal alcohol.

In accordance with this invention the preparation of the tertiary aralkyl urethane ester takes place at temperatures from 40° C. up to 150° C. in the presence of an acid catalyst, such as sulfuric acid, toluene sulfonic acid, dodecyl benzene sulfonic acid, hydrocarbon sulfate esters, hydrochloric acid, boron trifluoride and other Lewis and Bronstead acids. The reaction can take place in the absence of solvent or in the presence of solvents, such as methylene dichloride, toluene, xylene, chlorobenzene, and so forth.

Generally, the proportion of carbamic acid ester to olefin is in excess of stoichiometric. Preferably the carbamate is in substantial excess and functions as solvent and catalyst moderator as well as reactant. It is preferred in accordance with this invention to use from 50% to 800% stoichiometric excess of carbamate.

The amount of catalyst required to promote the addition of tertiary aralkyl olefin and carbamic acid ester is not critical and can be varied widely. Where substantial excess of carbamic acid ester is utilized the amount of catalyst, based on the olefin, is typically 0.01 and 10 mole% and preferably about 2 mole %.

Preferably the carbamate is heated mildly to maintain it molten, from 40° to 150° C. being preferred. The catalyst is dissolved in the molten carbamate, and the olefin is then slowly added. When the reaction is complete, the mixture is treated to remove or neutralize the catalyst. Unreacted carbamate ester is then removed by distillation.

Tertiary aralkyl urethane esters in accordance with this invention form the corresponding isocyanate by thermal cracking while splitting off the alkanol. In many cases the alcohol can usefully be recycled by reaction with urea or isocyanic acid (HNCO) to form the starting carbamate ester. In addition to their utility in the formation of the corresponding isocyanates the tertiary aralkyl urethane esters of this invention may also be useful for other purposes. For example, some of these compounds are quite similar to known herbicides, and herbicidal activity is anticipated. The urethane esters of higher alkanols can also be used as blocked isocyanates in powder coatings and the like.

In cracking the urethane esters according to this invention to form the corresponding isocyanates the catalyst must be removed or neutralized for example, with calcium oxide, sodium carbonate, sodium hydroxide and the like, which is followed by cracking of the urethane ester either neat or in high boiling solvents, such as hexadecane, diphenyl ether, diisopropyl naphthalene and the like. Cracking takes place at temperatures on the order of 150° to 350° C. splitting off the alkanol to yield the corresponding isocyanate.

This invention has particular application in the production of tertiary aralkyl polyisocyanates from polyolefins and carbamic acid esters by addition of the reactants to form the corresponding polyurethane esters followed by thermal cracking of the polyurethane esters to the corresponding polyisocyanates. Polyolefin reactants which are contemplated include diisopropenyl benzenes (DIPEB), triisopropenylbenzene and diisopropenyl naphthalenes, all of which yield highly desirable polyisocyanates. The addition reaction can also be utilized with diolefins, such as a diisopropenylbenzene, to favor the production of a monourethane, such as isopropenyl-α,α-dimethylbenzyl urethane (TMU), which can be thermally cracked to the corresponding olefinic monoisocyanate, such as isopropenyl-α,α-dimethylbenzyl isocyanate (TMI).

The thermal cracking of tertiary aralkyl polyurethanes derived by an acid promoted addition reaction to form the corresponding isocyanates is particularly surprising in view of the instability of such urethanes in the presence of even a small amount of acid Polyurethanes, such as tetramethylxylylene diurethane (TMXDU) crack extensively in the presence of traces of acid to form monoisocyanates and other undesired products. It is, therefore, also a feature of the invention that the urethane esters are thermally cracked only after complete neutralization of the acid catalyst. By "complete neutralization" it should be understood that the amount of alkali or alkaline material, such as calcium oxide, sodium hydroxide, sodium carbonate or the like, is not just in excess of the stoichiometric quantity but is sufficient to bring the pH of the mixture substantially to 7 or higher. Neutralization should be carried out before recovery steps, such as removal of the excess carbamic acid ester after which the urethane ester can be cracked.

The following Examples illustrate the preparation of urethane esters in accordance with this invention and the utilization of such esters in the preparation of isocyanates useful in preparation of polyurethanes.

EXAMPLE 1

A mixture containing 28.76 g (383.10 mmoles) of methyl carbamate, 8.8 ml of 1.08 M p-toluenesulfonic acid (9.50 mmoles) in toluene solution and 40 ml of methylene chloride was stirred at 45° C. until all solid was dissolved. Meta-diisopropenyl benzene (m-DIPEB) (15.19 g, 96.1 mmoles) was then added dropwise into the solution. After stirring at 45° C. for 22 hours, the reaction mixture was cooled to room temperature, washed with 10% aqueous sodium carbonate solution, and the organic layer dried over sodium sulfate. Analysis by GLC (heneicosane, $C_{21}H_{44}$, internal standard) indicates a 67% yield of α,α,α',α'-tetramethyl-meta-xylylene diurethane (m-TMXDU) and a 20% yield of the methyl ester of m-isopropenyl-α,α-dimethyl-benzyl urethane (TMU).

Concentration of the resulting methylene chloride reaction mixture was carried out at reduced pressure. An equal volume of hexane was then added to precipitate the dimethyl ester m-TMXDU, giving a white solid which was collected by filtration (mp 128°–130° C.; yield: 44% m-TMU). The remainder of the m-TMXDU in the methylene chloride-hexane solution could be isolated by further evaporation of methylene chloride solvent, followed by the addition of more hexane to the oily residue.

EXAMPLE 2

To a flask containing 59.30 g (789.92 mmoles) of molten methyl carbamate (85° C. oil bath) was added 260 mg (2.6 mmole) of conc.sulfuric acid. The temperature of the oil bath was then lowered to 60° C., and 14.79 g (93.61 mmoles) of m-DIPEB added dropwise to the reaction mixture. The reaction mixture was stirred 60° C. for 4.5 hours, and 500 mg of anhydrous sodium carbonate added to neutralize the acid catalyst. The mixture was stirred at 60° C. for another 30 minutes and then distilled under the vacuum 95°/30 mm Hg) to recover unreacted methyl carbamate (44.05 g; >90% recovery). GLC analyses of the white residue showed that m-TMXDU and m-TMU were formed in 65% and 24% yields, respectively. The solid was then mixed with 50 g of hexadecane and 1.66 g of heneicosane (GLC internal standard), and the mixture cracked at 265° C. for 4 hours. GLC analyses indicated that α,α,α'-,α'-tetramethyl meta-xylene diisocyanate (m-TMXDI) (45%), meta-isopropenyldimethylbenzene isocyanate (m-TMI) (10%) and α,α,α',α'-tetramethyl-meta-xylene monourethane monoisocyanate (m-TMXUI) (3%) were formed based on the m-DIPEB.

EXAMPLE 3

To a flask containing 59.30 g (787.92 mmoles) of molten methyl carbamate (85° C. oil bath) was added 260 mg (2.6 mmoles) of concentrated sulfuric acid. The temperature of the reaction mixture was then lowered to 60° C. and 14.79 g (93.61 mmoles) of p-DIPEB added dropwise to the reaction mixture. The reaction mixture was stirred for 4.5 hours at 60°, and 1 g CaO added to neutralize the acid catalyst. The reaction mixture was stirred for another 30 minutes at 60° C. and distilled under vacuum (95°/30 mm Hg) to recover unreacted methyl carbamate (45.0 g; >90% recovery). GLC analysis of the residue showed that 69% p-TMXDU and 21% p-TMU had formed.

The resultant mixture was then cracked by the treatment described for the corresponding meta-compounds in Example 2. GLC analysis gave 62% p-TMXDI and 16% p-TMI based on the p-DIPEB.

EXAMPLE 4

By way of further examples of the thermal cracking of diurethane, a mixture containing 25.15 g of p-TMXDU (81.6 mmoles), 100 g of hexadecane and 14.25 g of heneicosane (an inert internal standard) was heated with stirring in a 265° C. oil bath in a slow stream of nitrogen. Methanol evolved was collected in a dry-ice acetone cold trap. Heating continued for 4 hours, and the reaction mixture analyzed with GLC and IR after cooling to room temperature. Both GLC and IR analysis confirmed the formation of p-TMXDI, p-TMXUI (mono-urethane-monoisocyanate) and p-TMI (mono-isopropenyl-monoisocyanate). GLC (internal standard method) indicated yields were 68%, 20% and 6%, respectively. The liquid collected in the cold trap weighed 4.57 g, and was mostly methanol, as indicated by IR analyses.

EXAMPLES 5-27

Although the preceding examples have been confined to urethanes produced by reaction of tertiary aralkyl olefins with methyl carbamate, urethanes which are esters of other lower alkanols, particularly straight chain alkanols, are useful in preparing isocyanates by thermal cracking following the procedures generally outlined above. A number of such urethane esters have been prepared and are described in TABLE I.

TABLE I

| EX. NO. | URETHANE ESTER | ALKANOL RESIDUE | APPEARANCE |
|---|---|---|---|
| 5 | 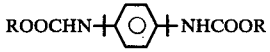 | methyl | white solid |
| 6 | " | ethyl | white fluffy needles |
| 7 | " | n-propyl | white needles |
| 8 | " | iso-propyl | white powder |
| 9 | " | n-butyl | white powder |
| 10 | " | 2-ethylhexyl | white powder |
| 11 | " | cyclohexyl | white powder |
| 12 | 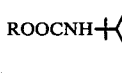 | methyl | white crystalline powder |
| 13 | " | ethyl | white needles (fine) |
| 14 | " | n-propyl | fine white needles |
| 15 | " | iso-propyl | white powder |
| 16 | " | n-butyl | white crystals solid |
| 17 | " | benzyl | white solid |
| 18 | " | n-octadecyl | white solid |
| 19 | 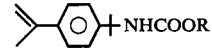 | methyl | white solid |
| 20 | 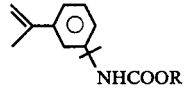 | methyl | oil |
| 21 | " | ethyl | oil |
| 22 | " | m-propyl | oil |
| 23 | " | iso-propyl | oil |
| 24 | " | n-butyl | oil |
| 25 | " | benzyl | oil |
| 26 | " | n-octadecyl | white solid |
| 27 | 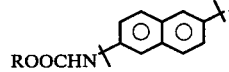 | methyl | white solid |

| EX. NO. | M.P., °C. | NMR δ-VALUE (CDCl₃) (60-MHz) |
|---|---|---|
| 5 | 182-184 | 1.6(12H,S,CH$_3$);3.5(6H,S,O—CH$_3$);5.1(2H,bS,NH); 7.25(4H,S,aro) |
| 6 | 159-160 | 1.15(6H,t J = 7Hz);1.64(12H,S);3.98(4H,q J = 7Hz); 5.05(2H,bs);7.30(4H,S) |
| 7 | 170-173 | 0.83(6H,t J = 7Hz);1.2-1.8(4H,m J ≃ 7Hz);1.65(12H,S); 3.88(4H,t J = 7Hz);5.03(2H,bS);7.25(4H,S) |
| 8 | 196-197 | 1.12(12H,d J = 6.5Hz);1.65(12H,S);4.77(2H,septet J = 6.5Hz);4.97(2H,bS);7.30(4H,S) |
| 9 | 132-133.5 | 0.86(6H,t J ≃ 6Hz);1.0-1.8(8H,m),1.65(12H,S);3.91 (4H,t J ≃ 6Hz);5.00(2H,bS);7.22(4H,S) |
| 10 | 97-98 | 0.86-1.8(30H,m);1.63(12H,S);3.86(4H,d J ≃ 4.5Hz); 5.00(2H,bS);7.25(4H,S) |
| 11 | 202-204 | 1.0-1.9(22H,m);1.63(12H,S);4.5(2H,m);4.93(2H,bS); |

TABLE I-continued

| | | |
|---|---|---|
| | | 7.23(4H,S) |
| 12 | 130–132 | 1.66(12H,S);3.55(6H,S);5.10(2H,bS);7.20(3H,m)7.33 (1H,m) |
| 13 | 101–103 | 1.14(6H,t J = 7Hz);1.64(12H,S);3.97(4H,q J = 7Hz); 5.02(2H,bS);7.15(3H,S);7.30(1H,m) |
| 14 | 94–95.5 | 0.83(6H,t J ≃ 6.5Hz);1.2–1.8(4H,m);1.63(12H,S); 3.85(4H,t J ≃ 6.5Hz);4.98(2H,bS);7.13(3H,m);7.28(1H,m) |
| 15 | 105–107.5 | 1.12(12H,d J ≃ 6Hz);1.63(12H,S);4.73(2H,septet); 4.93(2H,bS);7.12(3H,m);7.27(1H,m) |
| 16 | 64–66.5 | 0.86(6H,t J ≃ 6Hz);1.1–1.8(8H,m);1.64(12H,S); 3.90(4H,t J ≃ 6Hz);4.98(2H,bS);7.17(3H,m);7.27(1H,m); |
| 17 | 82–84 | |
| 18 | 47–49 | |
| 19 | 56–57 | 1.65(6H,S);2.12(3H,dd J$_1$ ≃ 1.6,J$_2$ = .8Hz);3.53(3H,S); 4.97(1H,dq J$_1$ ≃ J$_2$ ≃ 1.6Hz);5.05(1H,bS);5.25(1H,dq J$_1$ ≃ 1.6,J$_2$ ≃ 0.8);7.25(4H,S) |
| 20 | bp 115 at 1mm | 1.55(6H,S);2.05(3H,dd);3.45(3H,S);4.95(1H,dq); 5.25(1H,bS);5.65(1H,dq);7.16(3H,m);7.40(1H,m) |
| 21 | — | 1.13(3H,t J = 7z);1.64(6H,S);2.10(3H,dd);3.95 (2H,q J = 7Hz);4.97(1H,dq);5.03(1H,bS);5.20(1H,dq): 7.13(3H,m);7.32(1H,m) |
| 22 | — | 0.82(3H,t J — 7z);1.2–1.8(2H,m);1.65(6H,S);2.10 (3H,dd);3.85(2H,t J = 7Hz);4.97(1H,dq);5.02(1H,bS); 5.20(1H,dq);7.14(3H,m);7.30(1H,m) |
| 23 | — | 1.12(6H,d J ≃ 6Hz);1.63(6H,S);2.12(3H,dd J ≃ 1.6 J$_2$ ≃ 0.8;4.74(1H,septet);4.98(1H,dq J$_1$ ≃ J$_2$ ≃ 1.6); 5.03(1H,bS);5.23(1H,dq J$_1$ ≃ 1.6,J$_2$ ≃ 0.8);7.17(3H,m); 7.35(1H,m) |
| 24 | — | 0.85(3H,t);1.1–1.8(4H,m);1.65(6H,S);2.12(3H,dd); 3.90(2H,t);4.97(1H,dq);5.10(1H,bS);5.23(1H,dq); 7.17(3H,m);7.23(1H,m) |
| 25 | — | |
| 26 | 78–81 | |
| 27 | 177–178 | 7.50(bm,3,Ar),5.15(bs,1,NH),3.52(S,3,OCH$_3$,1.70 (S,6,CH$_3$) |

In Table I the urethane esters of alkanols other than methanol were prepared by reaction of the alkanol and the corresponding isocyanate, rather than by the addition reaction of carbamate ester and olefin. The addition reaction can, however, be employed to prepare these urethanes also. Yields of diurethanes are not as good as yields of monourethanes. The yields also are reduced as higher alkanols are used. Yields are generally better with normal alkanol esters of carbamic acid.

In a commercial processing arrangement the olefinic monourethane product TMU can be recycled with DIPEB in addition reaction with methyl carbamate. The two urethanes TMXDU and TMU are difficult to separate, however; and recycle of the TMU is not practicable. The thermally cracked product of the monourethanes, the isopropenyl monoisocyanate TMI, moreover, can not be recycled directly as it will not react with methyl carbamate under the reaction conditions for DIPEB and carbamate ester. Nevertheless, where this product is not desired for other purposes it can be reacted with methanol to reform the isopropenyl-monourethanne TMU for recycle with DIPEB. The monourethane-monoisocyanate product of the thermal cracking stage can, of course, be recycled for additional thermal cracking. The following are Examples:

EXAMPLE 28 m-DIPEB was slowly added to molten mixture of methyl carbamate (mc) and concentrated sulfuric acid maintained at 60° C. (mole ratio of m-DIPEB: MC: H$_2$SO$_4$=1:8:0.025, respectively) After the addition of DIPEB, the reaction mixture was stirred for 4–5 hours, and 300% mole excess solid sodium carbonate relative to sulfuric acid was added to basify the mixture. The mixture was stirred at 60° C. for a half hour more and the reaction mixture vacuum distilled (approx. 80°/20 mm.) to recover unreacted methyl carbamate (>90% recovered). To the distillate residue which contained m-TMU (24% yield) and m-TMXDU (65% yield) was added 10% by weight of finely divided CaO. The mixture was heated at 200° at 20 mmHg. for 90 minutes to crack the urethanes to m-TMXDI and m-TMI. At the end of the cracking cycle, the vacuum was decreased to 10 mm and m-TMXDI and m-TMI collected by fractional distillation.

The m-TMI collected was recycled as described above, by first converting it to m-TMU by reaction with methanol.

EXAMPLE 29

A solution containing 34.2 g (170 mmoles) of m-TMI, 100 ml of methanol and 50 mg of dibutyltin dilaurate was heated with stirring in a 70° C. oil bath for 3 hours. The reaction mixture was then cooled to room temperature, and the excess methanol was removed at reduced pressure. The residue, an oil, was distilled under vacuum to yield 34.2 grams of m-TMU (bp 115° C., 1 mm Hg).

EXAMPLE 30 m-TMU 5 g (22 mmoles) was slowly added to a molten mixture of methyl carbamate (13.2 g; 176 mmoles) containing 0.26 g (2.6 mmoles) of concentrated sulfuric acid at 70° C. The mixture was heated for three hours at 70°, and analyzed by GLC in the usual manner. Analysis showed an 84% yield of m-TMXDU with 15% m-TMU unreacted.

EXAMPLE 31

To a molten mixture of 20.0 g (266.4 mmoles) of methyl carbamate and 100 mg (1 mmole) of conc. sulfuric acid maintained at 65° C. (oil bath) was added 5.2 g (32.9 mmoles) of m-DIPEB and 2.4 g (10.3 mmoles) of m-TMU. After the addition was completed, the reaction was stirred at 65° C. for 3 hours. and analyzed by GLC. Analysis indicated that the area percent ratio of m-TMXDU to m-TMU was the same as that observed in the m-DIPEB-methyl carbamate reaction (4~5:1). The yields of m-TMXDU and m-TMU were 72 and 18% respectively.

EXAMPLE 32

A processing arrangement for production of TMXDI based on the preceding examples, particularly 29–31, is illustrated in the accompanying drawing which is a flow diagram.

As shown in the drawing, there are four basic steps involved in the production of TMXDI from DIPEB and the methyl ester of carbamic acid. These are the addition reaction of the carbamate and diolefin, indicated by the reference numeral 10; neutralization of the acid catalyst with base, indicated by the reference numeral 20; stripping of the methyl carbamate, indicated by the reference numeral 30; and thermal cracking of the resultant urethanes to TMXDI and other products, indicated by the reference numeral 40.

In this process the two basic ingredients, DIPEB and methyl carbamate are introduced at addition step 10, as indicated by flow lines 11 and 12. Catalyst, such as sulfuric acid, is also introduced as indicated by the reference numeral 13. Recycled TMU subsequently formed during the process is, as shown by flow line 15, is also introduced at addition step 10.

The product of olefin addition step 10 is admixed with base, such as sodium carbonate in the neutralization step 20, as indicated by flow lines 21 and 22 respectively. The neutralized material, as indicated by flow line 31, is then stripped of methyl carbamate at step 30 to recover methyl carbamate which via line 14 is recycled to addition step 10 with make-up methyl carbamate indicated by line 16. After stripping the methyl carbamate, the product as indicated by flow line 41 consisting basically of TMXDU, TMU and polymerized material, is then treated at cracking step 40. TMI and methyl alcohol are recovered in cracking step 40 as indicated by the flow lines 51 and 52, respectively. The desired product TMXDI is recovered from cracking step 40 as indicated by flow line 43, and still bottoms from cracking step 40 are indicated by flow line 44.

To the extent by-product TMI can not be used as such it is reacted with the recovered methanol by a process 50 such as described in Example 29 to convert the olefinic TMI to TMU, which then is recycled to the addition step, as indicated by flow line 15, for further reaction with methyl carbamate.

An important aspect of the recycle of TMU is that the product distribution in olefin addition step 10 is not affected by the presence of the added olefinic TMU. Thus the recycle of TMI as TMU greatly improves the efficiency in conversion of DIPEB to TMXDI.

We claim:

1. Urethanes selected from urethanes having the formulae:

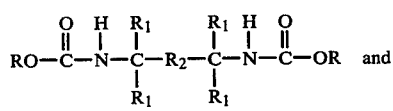 and

-continued

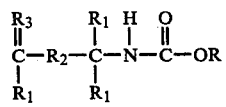

wherein
R is an alkyl radical having from 1 to 18 carbon atoms;
$R_1$ is an alkyl radical having from 1 to 3 carbon atoms;
$R_2$ represents an aromatic hydrocarbon moiety selected from phenyl, biphenyl and naphthalyl groups and such groups having halo, methyl and methoxy substituents and substituents of the formula:

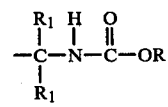

and wherein $R_3$ is an alkylidene radical having from 1 to 3 carbon atoms.

2. A urethane according to claim 1 in which $R_2$ is a benzo group.
3. A urethane according to claim 1 in which $R_2$ is a naphtho group.
4. The alkyl esters of $\alpha,\alpha,\alpha',\alpha'$-tetramethyl-meta-xylylene dicarbamic acid.
5. The dialkyl esters of $\alpha,\alpha,\alpha',\alpha'$-tetramethyl-paraxylylene dicarbamic acid.
6. A dimethyl ester according to claim 5.
7. A diisopropyl ester according to claim 5.
8. The alkyl esters of isopropenyl cumyl carbamic acid.
9. A methyl ester according to claim 8.
10. An isopropyl ester according to claim 8.
11. A benzyl ester according to claim 8.
12. An octadecyl ester according to claim 8.
13. In a process for production of urethanes of the general formula:

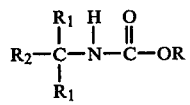

where
R is an alkyl radical derived from a lower alkanol;
$R_1$ is an alkyl radical having from 1 to 3 carbon atoms; and
$R_2$ represents an aromatic hydrocarbon moiety selected from phenyl, biphenyl and naphthalyl groups and such groups having halo, methyl and methoxy substituents and substituents of the formula:

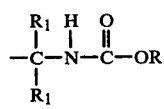

wherein R and $R_1$ have the same significance, by addition of the corresponding olefin and a carbamic acid ester of a lower alkanol in the presence of moderate heat and an acid catalyst, the improvement which comprises forming a mixture consisting essentially of said catalyst and said carbamic acid ester at a temperature between 40° and 150° C. at which said carbamic acid ester is molten and thereafter adding said olefin to said mixture to react said carbamic acid ester and olefin to form said urethane.

14. The improvement according to claim 13 in which said olefin is added to said mixture dropwise, the olefin is a diisopropenyl benzene and the carbamic acid ester is methyl carbamate.

15. The improvement according to claim 13, or 14 in which said mixture and added olefin are neutralized after formation of said urethane.

16. The improvement according to claim 13 in which said carbamic acid ester is in excess of the amount of olefin required to form said urethane, in which said mixture and added olefin are neutralized after formation of said urethane, and in which excess, unreacted carbamic acid ester is removed after neutralization.

17. A process for the production of tertiary aralkyl isocyanates which comprises heating a urethane of the formulae.

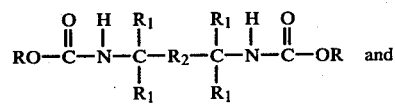

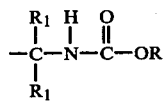

wherein
R is an alkyl radical derived from a lower alkanol;
$R_1$ is an alkyl radical having from 1 to 3 carbon atoms; and
$R_2$ is an aromatic hydrocarbon moiety selected from phenyl, biphenyl and naphthalyl groups and such groups having halo, methyl and methoxy substituents and substituents and substituents of the formula:

$$\begin{array}{c} R_1 \ H \ O \\ | \ \ | \ \ || \\ -C-N-C-OR \\ | \\ R_1 \end{array}$$

and wherein $R_3$ is an alkylidene group having from one to three carbon atoms, said urethane being heated at 200°–300° for a sufficient time to split off the alkanol of the formula ROH and form the isocyanate corresponding to said urethane.

18. A process for production of α,α,α',α'-tetramethyl xylylene diisocyanates which comprises:
a. reacting a diisopropenyl benzene and isopropenyl-α,α-dimethylbenzyl urethane with an excess of methyl carbamate in the presence of moderate heat and an acid catalyst to convert the olefins to urethanes,
b. neutralizing said catalyst in the resultant mixture,
c. stripping unreacted methyl carbamate from the neutralized mixture,
d. thermally cracking the stripped mixture to convert urethanes to isocyanates whereby a mixture including tetramethyl xylene diisocyanate and isopropenyl dimethylbenzyl isocyanate is obtained,
e. recovering methanol from said mixture during thermal cracking,
f. separating isopropenyl-dimethylbenzyl isocyanate and tetramethyl xylylene diisocyanate from the cracked mixture,
g. reacting said isopropenyl dimethylbenzyl isocyanate and methanol to form isopropenyl-dimethylbenzyl urethane and,
h. recycling said isopropenyl-dimethylbenzyl urethane so formed and said stripped methyl carbamate to said reaction with diisopropenyl benzene.

19. The diethyl ester according to claim 5.

20. An ethyl ester according to claim 8.

21. The improvement according to claim 13 wherein said olefin is added to the mixture dropwise, the olefin is a diisopropenyl benzene and the carbamic acid ester is alkyl carbamate.

22. The improvement according to claim 16 wherein said mixture and added olefin are neutralized to complete neutralization.

23. A process for the production of α, α, α', α'-tetramethyl xylylene diisocyanates which comprises:
a. reacting a diisopropenyl benzene and isopropenyl α, α- dimethylbenzyl urethane with an excess of alkyl carbamate in the presence of moderate heat and an acid catalyst to convert the olefins to urethanes,
b. neutralizing said catalyst in the resultant mixture,
c. stripping unreacted alkyl carbamate from the neutralized mixture,
d. thermally cracking the stripped mixture to convert urethanes to isocyanates whereby a mixture including tetramethyl xylylene diisocyanate and isopropenyl isocyanate is obtained,
e. recovering alkanol from said mixture during thermal cracking,
f. separating isopropenyl-dimethylbenzyl isocyanate and tetramethyl xylylene diisocyanate from the cracked mixture,
g. reacting said isopropenyl dimethylbenzyl isocyanate and alkanol to form isopropenyl-dimethylbenzyl urethane, and
h. recycling said isopropenyl-dimethylbenzyl urethane so formed and said stripped methyl carbamate to said reaction with diisopropenyl benzene.

24. A process according to claim 23 wherein said alkyl carbamate is isopropyl carbamate.

25. A process according to claim 23 wherein said alkyl carbamate is ethyl carbamate.

* * * * *

UNITED STATES PATENT OFFICE
CERTIFICATE OF CORRECTION

Patent No. 4,439,616             Dated March 27, 1984

Inventor(s) Balwant Singh, Peter Forgione, and Laurence Chang

It is certified that error appears in the above-identified patent and that said Letters Patent are hereby corrected as shown below:

In Column 10 (Claim 1), line 9, after "atoms" insert -- , or is aralkyl --.

In Column 10 (Claim 13), line 50, after "alkanol" insert -- , or is aralkyl --.

In Column 11 (Claim 17), line 42, delete "and substituents".

In Column 11 (Claim 17), line 52, after "-300°" insert -- C --.

Signed and Sealed this

Second Day of April 1985

[SEAL]

Attest:

DONALD J. QUIGG

Attesting Officer          Acting Commissioner of Patents and Trademarks